(12) United States Patent
McConnell et al.

(10) Patent No.: US 10,835,545 B2
(45) Date of Patent: *Nov. 17, 2020

(54) SYNTHETIC COMPOSITION AND METHOD FOR MODULATING BRAIN FUNCTION AND BEHAVIOUR

(71) Applicant: GLYCOM A/S, Hørsholm (DK)

(72) Inventors: Bruce McConnell, La Tour de Peilz (CH); Emma Elison, Hjärup (SE); Louise Kristine Vigsnæs, Copenhagen NV (DK)

(73) Assignee: GLYCOM A/S, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/771,189

(22) PCT Filed: Oct. 28, 2016

(86) PCT No.: PCT/DK2016/050344
§ 371 (c)(1),
(2) Date: Apr. 26, 2018

(87) PCT Pub. No.: WO2017/071715
PCT Pub. Date: May 4, 2017

(65) Prior Publication Data
US 2018/0369260 A1 Dec. 27, 2018

(30) Foreign Application Priority Data

Oct. 28, 2015 (DK) .................................. 2015 70696
Feb. 24, 2016 (DK) .................................. 2016 70100

(51) Int. Cl.
| | | |
|---|---|---|
| *A61K 31/702* | (2006.01) | |
| *C07H 3/06* | (2006.01) | |
| *A23L 33/15* | (2016.01) | |
| *A61P 25/22* | (2006.01) | |
| *A61P 25/24* | (2006.01) | |
| *A61P 1/00* | (2006.01) | |

(52) U.S. Cl.
CPC ............ *A61K 31/702* (2013.01); *A23L 33/15* (2016.08); *A61P 1/00* (2018.01); *A61P 25/22* (2018.01); *A61P 25/24* (2018.01); *C07H 3/06* (2013.01)

(58) Field of Classification Search
None
See application file for complete search history.

(56) References Cited

U.S. PATENT DOCUMENTS

| | | | |
|---|---|---|---|
| 9,034,847 B2 * | 5/2015 | Morrow ............... | A61K 31/702 514/61 |
| 2012/0171165 A1 | 7/2012 | Buck et al. | |
| 2012/0208782 A1 | 8/2012 | Frantz | |
| 2015/0265661 A1 | 9/2015 | Newburg et al. | |
| 2015/0305384 A1 | 10/2015 | Chichlowski et al. | |
| 2016/0243139 A1 | 8/2016 | Vigsnæs et al. | |
| 2016/0287637 A1 | 10/2016 | McConnell et al. | |
| 2018/0169122 A1 * | 6/2018 | Hennet ............... | A61K 31/7004 |
| 2018/0177809 A1 * | 6/2018 | McConnell ........... | A61K 31/702 |

FOREIGN PATENT DOCUMENTS

| | | |
|---|---|---|
| EP | 2708145 A1 | 3/2014 |
| EP | 2708147 A1 | 3/2014 |
| EP | 2842560 A1 | 4/2015 |
| WO | 0104341 A1 | 1/2001 |
| WO | 2007101862 A1 | 9/2007 |
| WO | 2010115934 A1 | 10/2010 |
| WO | 2010115935 A1 | 10/2010 |
| WO | 2011023689 A1 | 3/2011 |
| WO | 2011100980 A1 | 8/2011 |
| WO | 2012007588 A9 | 1/2012 |
| WO | 2012089783 A1 | 7/2012 |
| WO | 2012113404 A1 | 8/2012 |
| WO | 2012113405 A1 | 8/2012 |
| WO | 2012127410 A1 | 9/2012 |
| WO | 2012155916 A1 | 11/2012 |
| WO | 2012156897 A1 | 11/2012 |
| WO | 2012156898 A1 | 11/2012 |
| WO | 2013032674 A1 | 3/2013 |
| WO | 2013044928 A1 | 4/2013 |
| WO | 2013091660 A1 | 6/2013 |
| WO | 2013139344 A1 | 9/2013 |
| WO | 2014100126 A1 | 6/2014 |
| WO | 2014100191 A1 | 6/2014 |
| WO | WO2014/100126 * | 6/2014 ............ A23L 1/308 |
| WO | 2014164882 A1 | 10/2014 |
| WO | 2015157098 A1 | 10/2015 |

(Continued)

OTHER PUBLICATIONS

Fond et al., "Anxiety and depression comorbidities in irritable bowel syndrome (IBS): a systematic review and meta-analysis" Eur Arch Psychiatry Clin Neurosci vol. 264, pp. 651-660 (Year: 2014).*
Silk et al., "Clinical trial: the effects of a trans-galactooligosaccharide prebiotic on faecal microbiota and symptoms in irritable bowel syndrome" Aliment Pharmacol Ther vol. 29 pp. 508-518 (Year: 2009).*
Coulet et al., "Pre-clinical safety evaluation of the synthetic human milk, nature-identical, oligosaccharide 2␣-O-Fucosyllactose (2␣FL)" Regulatory Technology and Pharmacology (2014) vol. 68 pp. 59-69 (Year: 2014).*
Wang et al., "Enzymatic production of HMO mimics by the sialylation of galacto-oligosaccharides" Food Chemistry vol. 181 pp. 51-56 (Year: 2015).*

(Continued)

*Primary Examiner* — Eric Olson
(74) *Attorney, Agent, or Firm* — Neal, Gerber & Eisenberg LLP

(57) ABSTRACT

A synthetic composition for use in improving one or more co-morbid mental disorder symptoms of a patient with IBS, characterised in that the composition contains an effective amount of one or more neutral human milk oligosaccharides, is disclosed.

21 Claims, No Drawings

(56) References Cited

FOREIGN PATENT DOCUMENTS

| WO | 2016066175 A1 | 5/2016 |
|---|---|---|
| WO | 2017071716 A1 | 5/2017 |

OTHER PUBLICATIONS

LoCasio et al., "A versatile and scalable strategy for glycoprofiling bifidobacterial consumption of human milk oligosaccharides" vol. 2 No. 3 pp. 333-342 (Year: 2009).*

Ward et al., "In vitro fermentability of human milk oligosaccharides by several strains of bifidobacteria" vol. 51 pp. 1398-1405 (Year: 2007).*

Barbara, G. et al., "Mast Cell-Dependent Excitation of Visceral-Nociceptive Sensory Neurons in Irritable Bowel Syndrome," Gastroenterology, 2007, vol. 132, pp. 26-37.

Bottacini, F. et al., "Diversity, ecology and intestinal function of bifidobacteria," Microbial Cell Factories, 2014, vol. 13, 15 pages.

Chen, X., "Human Milk Oligosaccharides (HMOS): Structure, Function, and Enzyme-Catalyzed Synthesis," Advances in Carbohydrate Chemistry and Biochemistry, 2015, vol. 72, pp. 113-190.

Collins, S.M. et al., "The Relationship Between Intestinal Microbiota and the Central Nervous System in Normal Gastrointestinal Function and Disease," Gastroenterology, 2009, vol. 136, pp. 2003-2014.

Dinan, T.G. et al., "Psychobiotics: A Novel Class of Psychotropic," Biol Psychiatry, 2013, vol. 74, pp. 720-726.

Duranti, S. et al., "Exploration of the Genomic Diversity and Core Genome of the Bifidobacterium adolescentis Phylogenetic Group by Means of a Polyphasic Approach," Applied and Environmental Microbiology, 2013, vol. 79(1), pp. 336-346.

Ferrari, A.J. et al., "Burden of Depressive Disorders by Country, Sex, Age, and Year: Findings from the Global Burden of Disease Study 2010," PLOW Medicine, 2013, vol. 10(11), 12 pages.

Kendler, K.S. et al., "Illicit psychoactive substance use, abuse and dependence in a population-based sample of Norwegian twins," Psychol Med., 2016, vol. 36(7), pp. 955-962.

Kim, G. et al., "Methanobrevibacter smithii Is the Predominant Methanogen in Patients with Constipation-Predominant IBS and Methane on Breath," Dig Dis Sci, 2012, vol. 57, pp. 3213-3218.

Longstreth, G.F. et al., "Functional Bowel Disorders," Gastroenterology, 2006, vol. 130, pp. 1480-1491.

Qin, J. et al., "A human gut microbial gene catalogue established by metagenomic sequencing," Nature, 2010, vol. 464, pp. 59-65.

Savignac, H.M. et al., "Bifidobacteria exert strain-specific effects on stress-related behavior and physiology in BALB/c mice," Neurogastroenterol Motil, 2014, vol. 26, pp. 1615-1627.

Tarr, A.J. et al., "The prebiotics 3'Sialyllactose and 6'Sialyllactose diminish stressor-induced anxiety-like behavior and colonic microbiota alterations: evidence for effects on the gut-brain axis", Brain Behav Immun., 2015, vol. 50, pp. 166-177.

Urashima, T. et al. (2011) Nutrition and Diet Research Progress: Milk Oligosaccharides. New York: Nova Science Publishers, Inc. 92 pages.

Depeint, F., et al., "Prebiotic evaluation of a novel galactooligosaccharide mixture produced by the enzymatic activity of Bifidobacterium bifidum NCIMB 41171, in healthy humans: a randomized, double-blind, crossover, placebo-controlled intervention study," Am J Clin Nutr 2008; 87:785-91.

* cited by examiner

SYNTHETIC COMPOSITION AND METHOD FOR MODULATING BRAIN FUNCTION AND BEHAVIOUR

CROSS-REFERENCE TO RELATED APPLICATION

This application is a national stage entry pursuant to 35 U.S.C. § 371 of International Application No. PCT/DK2016/050344, filed on Oct. 28, 2016, which claims priority to Denmark Patent Application No. PA 2015 70696, filed on Oct. 28, 2015, and. Denmark Patent Application No. PA 2016 70100, filed on Feb. 24, 2016, the contents of all of which are fully incorporated herein by reference.

FIELD OF THE INVENTION

This invention relates generally to compositions and methods for the treatment of disorders in brain functioning and behaviour in irritable bowel syndrome (IBS) patients, especially symptoms of co-morbid mental disorders.

BACKGROUND TO THE INVENTION

Irritable bowel syndrome is a clinically heterogeneous disorder of human, particularly adult, patients with chronic symptoms such as abdominal pain, abdominal discomfort, abdominal bloating, fatigue, and changes in bowel movement patterns, such as patterns of loose or more frequent bowel movements, diarrhoea and constipation. Routine clinical tests on patients typically show no abnormalities, although their bowels may be more sensitive to certain stimuli, such as balloon insufflation testing. The worldwide prevalence of IBS is about 10-20% (Longstreth et al. *Gastroenterology* 130, 1480 (2006)) but may be higher in certain countries. The causes of IBS are unknown but disruptions of the brain-gut axis, acute gastrointestinal infections, small intestinal bacterial overgrowths, antibiotic usages and dysbiosis are thought to be important risk factors (Kim et al. *Digest. Dis. Sci.* 57, 3213 (2012)). Chronic low-grade inflammation commonly occurs in IBS patients, but there are otherwise little or no observable clinical manifestations.

Diagnosis of IBS is difficult. No biomarker-based tests can be performed to diagnose IBS and therefore IBS is diagnosed clinically. Diagnosis generally involves positive clinical diagnosis using the Rome criteria. However, some clinicians diagnose by excluding conditions that produce IBS-like symptoms and then following a procedure to categorise a patient's symptoms. Once diagnosed, patients are usually classified in accordance with the Rome III criteria into four symptom subtypes based on stool consistency: diarrhoea predominant (IBS-D), constipation predominant (IBS-C), mixed subtype (IBS-M) with alternating episodes of both diarrhoea and constipation, and unsubtyped IBS (IBS-U).

There is no cure for IBS and current treatments focus on attempting to relieve symptoms. Treatments take various forms such as dietary adjustments, medication, and psychological interventions. Patient education and good doctor-patient relationships are also important. However, most treatment is unsatisfactory and most patients continue to experience chronic pain, fatigue, and other symptoms. While IBS has no direct effect on life expectancy, its high prevalence and significant effects on quality of life make it a condition with a high social cost. The general hopelessness associated with IBS is a source of frustration for both patients and health care practitioners treating them.

Current research has implicated the gastrointestinal microbiota in the pathophysiology of IBS. The human gastrointestinal microbiota includes at least 1000 different species of bacteria, which collectively make up to $10^{14}$ bacterial cells, tenfold the number of human cells, and they encode 100-fold more unique genes than the human genome (Qin et al. *Nature* 464, 59 (2010)). It is believed that an individual's genetic make-up and acquired immunity, as well as environmental factors, influence the composition of their gastrointestinal microbiota. The microbiota in turn shape the individual's immunity and physiology within the gastrointestinal system. Hence, regulated interaction between the gastrointestinal microbiota and host is important for colonic homeostasis, avoiding unnecessary reactions from the host's immune system. However, perturbation in this microbiota-immune interaction is believe to occur in individuals with IBS.

Many IBS patients exhibit co-morbid, brain-related disorders such as anxiety and depression. Brain-gut axis communication involving the neural, endocrine and immune systems is hypothesised to underlie these, and other, IBS symptoms (Collins et al. *Gastroenterology* 136, 2003 (2009)). However, a thorough understanding of the disorder is still emerging, which means that therapeutic strategies are limited. One arm of the brain-gut axis is the central efferent pathway, which is formed by the sympathetic nervous system and the hypothalamic-pituitary-adrenal axis (HPA). In stress-sensitive disorders including IBS, stress hormones of the HPA axis, such as adrenocorticotropic hormone (ACTH), cortisol, and catecholamine are released. Some studies have shown that the HPA axis response in IBS patients is caused by increased mucosal immune activation, which in turn increases plasma cytokine levels to stimulate the HPA axis. Further, subtle changes in mucosal immune cell populations, circulating cytokine profiles and mast cells have been identified in several studies in IBS patients. Moreover, mast cells in IBS biopsies appear to lie in closer proximity to colonic nerve endings and this strongly correlates with visceral pain sensitivity and brain disorders. These immune mediators may modulate GI motor and sensory neurons and muscle function resulting in the initiation and perpetuation of IBS symptoms (Barbara et al. *Gastroenterology*, 132, 25 (2007)).

IBS patients with symptoms of co-morbid mental disorders are usually treated, if treated at all, with psychotropic medication such as tricyclic antidepressants. However, this is off-label use and has a substantial side effect burden; not to mention social stigma. Other IBS medication targets symptoms such as constipation and diarrhoea and do not target the symptoms of co-morbid mental disorders.

Therefore, there remains a need for a generally safe and effective way for improving the brain functioning or behaviour symptoms of IBS patients.

SUMMARY OF THE INVENTION

In one aspect, this invention relates to one or more neutral human milk oligosaccharides ("neutral HMOs") for use in improving one or more co-morbid mental disorder symptoms of a patient with IBS, particularly a patient having one or more of stress, bacterial overgrowth, dysbiosis and an impaired mucosal barrier.

In another aspect, this invention provides a synthetic composition for use in improving one or more co-morbid mental disorder symptoms of a patient with IBS, particularly a patient having one or more of stress, bacterial overgrowth, dysbiosis and an impaired mucosal barrier, characterised in that the composition contains an effective amount of one or more neutral HMOs. The synthetic composition is preferably a nutritional composition.

In another aspect, this invention provides a method for treating a symptom of a co-morbid mental disorder in a patient with IBS, particularly a patient having one or more of stress, bacterial overgrowth, dysbiosis and an impaired mucosal barrier, the method comprising orally administering to the patient an effective amount of one or more neutral HMOs, preferably in the form of a synthetic composition. Preferably, the co-morbid mental disorder is anxiety and/or depression, and preferably both are reduced in the patient. Preferably, the abundance of bifidobacteria, more preferably a *Bifidobacterium* of the *B. adolescentis* phylogenetic group, especially *Bifidobacterium adolescentis* and/or *Bifidobacterium pseudocatenulatum*, is also increased in the colon of the IBS patient. Preferably, one or more of bacterial overgrowth, dysbiosis and impairment of mucosal barrier, is also reduced in the patient.

The patient can be administered a higher amount of the one or more neutral HMOs, preferably 5 g to 10 g per day, for an initial treatment period, followed by a lower amount, preferably 1 g to 5 g per day, for a maintenance period. The initial treatment period can be 1 to 8 weeks. The maintenance period is at least 1 month.

In a further aspect, this invention provides a use of one or more neutral HMOs, preferably in the form of a synthetic composition, for treating symptoms of one or more co-morbid mental disorders in a patient with IBS, particularly in a patient having one or more of stress, bacterial overgrowth, dysbiosis and an impaired mucosal barrier.

In all aspects, the neutral HMO is preferably selected from 2'-FL, 3-FL, DEL, LNT, LNnT, and LNFP-I. More preferably, the neutral HMO is a combination of one or more core HMOs and one or more fucosyl HMOs; for example, 2'-FL and/or DFL and LNnT and/or LNT. 2'-FL and/or DFL and LNnT and/or LNT may be present in a mass ratio of about 4:1 to 1:1; more preferably about 3:1 to 1:1.

DETAILED DESCRIPTION OF THE INVENTION

In accordance with this invention, it has been surprisingly found that neutral human milk oligosaccharides (neutral HMOs), advantageously 2'-FL, 3-FL, LNT, LNnT, LNFP-I and DEL, are able to improve co-morbid, brain-related disorders such as anxiety and depression in IBS patients, particularly those who are suffering from stress, bacterial overgrowth, dysbiosis or an impaired mucosal barrier. It is believed that the neutral HMOs can: (1) act as prebiotics to promote beneficial bacteria growth, especially bifidobacteria, and reduce bacterial overgrowth and dysbiosis; (2) act as decoys for pathogens by binding to them and thereby reduce/prevent binding of the pathogens to epithelial cells in the gastrointestinal tract; (3) act to reduce chronic mucosal inflammation; and/or (4) repair damage to the mucosal barrier. By reducing chronic mucosal inflammation including reducing mast cell degranulation, and/or repairing damage to the mucosal barrier, the neutral HMOs can also have beneficial effects on the enteric nervous systems of patients; potentially reducing anxiety and stress. Further, bifidobacteria, including *Bifidobacterium adolescentis*, are able to synthesize folate de novo, ensuring its constant bioavailability, and secrete neuromodulators such as gamma-aminobutyric acid (GABA), a potent inhibitory neurotransmitter involved is reducing stress, anxiety and depression. Folate can reduce depressive moods in certain patients; at least comparable to that of tricyclic antidepressants. Folate also appears to influence the rate of synthesis of tetrahydrobiopterin, a co-factor in the hydroxylation of phenylalanine and tryptophan, rate-limiting steps in the biosynthesis of dopamine, norepinephrine and serotonin, neurotransmitters postulated to play a role in the pathogenesis of depression. The intestinal bacteria may directly communicate with the central nervous system by way of the vagal sensory nerve fibres and the peripheral immune system.

Accordingly, neutral HMOs may be used to influence neurotransmission in the paraventricular hypothalamus, the central nucleus of the amygdala, and the bed nucleus of the stria terminalis. All three of these regions are involved in the processing of emotions related to anxiety and mood, and therefore the symptoms of emotional and mood disorders may be ameliorated by the treatment according to the invention.

Neutral HMOs for improving co-morbid, brain-related disorders as disclosed above can preferably be one or more fucosylated HMOs, or one or more non-fucosylated HMOs. In one embodiment, the neutral HMO is a mixture of neutral HMOs, even preferably a mixture comprising or consisting of a fucosylated and a non-fucosylated neutral HMO. Particularly, the mixture contains or consists of a fucosylated neutral HMO selected from the list consisting of 2'-FL, 3-FL, DFL and LNFP-I, and a non-fucosylated neutral HMO selected from the list consisting of LNT and LNnT. In one preferred embodiment, the mixture comprises or consists of 2'-FL and LNnT.

Embodiments of the invention are described using general terms and definitions of the following paragraphs. Still, in some cases, a term may be defined in the context of a particular embodiment.

According to the invention the term "patient" designates a non-infant human individual diagnosed with IBS. The term "non-infant" means an individual of any age above 3 years, e.g. it can be a child, a teenager, an adult or an elderly.

In accordance with this invention, the term "oral administration" preferably means any conventional form for the oral delivery of a composition to a patient that causes the deposition of the composition in the gastrointestinal tract (including the stomach) of the patient. Accordingly, oral administration includes swallowing of composition by the patient, enteral feeding through a naso-gastric tube, and the like.

Also herein, the term "effective amount" preferably means an amount of a composition that provides a neutral human milk oligosaccharide in a sufficient amount to render a desired treatment outcome in a patient. An effective amount can be administered in one or more doses to the patient to achieve the desired treatment outcome.

Also herein, the term "co-morbid mental disorder" preferably means a mental disorder associated with irritable bowel syndrome and involving an emotional disorder and/or a mood disorder. In this regard, the term "mood disorder" preferably means a mental disorder involving a primary disturbance of mood resulting in the mood being distorted or inconsistent with circumstances. Mood disorders include depression, major depressive disorder, dysthymia and bipolar disorder. The term "emotional disorder" preferably means a mental disorder involving a primary disturbance of emotion resulting in emotions being distorted or inconsistent with circumstances. Emotional disorders include excessive anxiety, fear, anger, happiness, etc. Co-morbid mental disorders include IBS-associated anxiety and IBS-associated depression.

Also herein, the term "neutral human milk oligosaccharide" or "neutral HMO" preferably means a complex carbohydrate found in human breast milk that is in neutral form (not acidic form). More than about 200 different HMO structures are known to exist in human breast milk (Urashima et al.: Milk Oligosaccharides, Nova Biomedical Books, New York, 2011; Chen *Adv. Carbohydr. Chem. Biochem.* 72, 113 (2015)). Neutral HMOs can be core and fucosylated oligosaccharides. Core HMOs are non-fucosylated neutral HMOs and consist of Glu, Gal and GlcNAc and are devoid of fucose and sialic acid. Examples of core HMOs include lacto-N-tetraose (LNT), lacto-N-neotetraose (LNnT), lacto-N-neohexaose (LNnH) lacto-N-hexaose (LNH) and para-lacto-N-neohexaose (pLNnH). Fucosyl HMOs are fucosylated lactoses or fucosylated core HMOs such as 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose III (LNFP-III), fucosyl-para-lacto-N-neohexaose (F-pLNnH), lacto-N-difucohexaose I (LNDFH-I), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-lacto-N-hexaose III (FLNH-III) and fucosyl-para-lacto-N-neohexaose (F-pLNnH).

Also herein, the terms "microbiota", "microflora" and "microbiome" preferably mean a community of living microorganisms that typically inhabits a human's, particularly an adult's, bodily organ(s) or part(s). The most dominant members of the gastrointestinal microbiota include microorganisms of the phyla of Firmicutes, Bacteroidetes, Actinobacteria, Proteobacteria, Synergistetes, Verrucomicrobia, Fusobacteria, and Euryarchaeota. At genus level the dominant microorganisms are *Bacteroides, Faecalibacterium, Bifidobacterium, Roseburia, Alistipes, Collinsella, Blautia, Coprococcus, Ruminococcus, Eubacterium* and *Dorea*; and at species level common species are *Bacteroides uniformis, Alistipes putredinis, Parabacteroides merdae, Ruminococcus bromii, Dorea fongicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. In some instances, the gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

Also herein, the term "*Bifidobacterium* of the *B. adolescentis* phylogenetic group" means a bacterium selected from a group consisting of *Bifidobacterium adolescentis, Bifidobacterium angulatum, Bifidobacterium catenulaturn, Bifidobacterium pseudocatenulatum, Bifidobacterium kashiwanohense, Bifidobacterium dentum* and *Bifidobacterium stercoris* (Duranti et al. *Appl. Environ. Microbiol.* 79, 336 (2013), Bottacini et al. *Microbial Cell Fact.* 13: S4 (2014)).

Also herein, the terms "irritable bowel syndrome" and "IBS" preferably mean a group of functional bowel disorders of humans, particularly adults, characterized by one or more chronic symptoms including abdominal pain, abdominal discomfort, abdominal bloating, fatigue, and changes in bowel movement patterns, such as patterns of loose or more frequent bowel movements, diarrhoea and constipation, typically in the absence of any apparent structural abnormality. There are at least three forms of IBS, depending on which symptom predominates: (1) diarrhoea-predominant (IBS-D); (2) constipation-predominant (IBS-C); and (3) IBS with alternating stool pattern (IBS-A). IBS can also occur in the form of a mixture of symptoms (IBS-M). There are also various clinical subtypes of IBS, such as post-infectious IBS (IBS-PI).

The neutral HMOs can be isolated or enriched by well-known processes from milk(s) secreted by mammals including, but not limited to human, bovine, ovine, porcine, or caprine species. The neutral HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, and mixtures of human milk oligosaccharides can be made as described in WO 2012/113405. As examples of enzymatic production, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 describes how to make core human milk oligosaccharides optionally substituted by fucose using genetically modified *E. coli*. If it is desired to additionally include acidic HMO's, these can be obtained as described in WO 2012/113404, WO 2012/007588, WO 01/04341 and WO 2007/101862.

The term "synthetic composition" designates a composition which is artificially prepared and preferably means a composition containing at least one compound that is produced ex vivo chemically and/or biologically, e.g. by means of chemical reaction, enzymatic reaction or recombinantly. The synthetic composition comprising one or more neutral human milk oligosaccharides can take any suitable form. In some embodiments a synthetic composition of the invention may be, but preferably is not, identical with a naturally occurring composition. For example, the composition can be in the form of a nutritional composition which contains other macronutrients such as proteins, lipids or other carbohydrates. The synthetic composition can also be a pharmaceutical composition. In one embodiment, the synthetic compositions contain one or more core HMOs and one or more fucosyl HMOs. In a preferred embodiment, the synthetic composition contains 2'-FL and/or DFL, and LNnT and/or LNT.

Nutritional Compositions

A nutritional composition can contain sources of protein, lipids and/or digestible carbohydrates and can be in powdered or liquid forms. The composition can be designed to be the sole source of nutrition or a nutritional supplement. For IBS patients, a nutritional supplement is preferred; especially a supplement which can form a meal or snack replacement. Preferably the nutritional composition is lactose-reduced or, better yet, lactose-free. Preferably, the nutritional composition is also free from, or low in amounts of, FODMAP carbohydrates.

Suitable protein sources include milk proteins, soy protein, rice protein, pea protein and oat protein, or mixtures thereof. Milk proteins can be in the form of milk protein concentrates, whey protein or casein, or mixtures of both. Soy, rice, pea and oat protein can be in the form or protein isolated. The protein can be whole protein or hydrolysed protein, either partially hydrolysed or extensively hydrolysed. The protein can provide about 5% to about 50%, preferably about 10% to 30%, of the energy of the nutritional composition. The protein source preferably is not a source of non-fermentable carbohydrates such as lactose. Therefore, if a milk protein is used as the protein source, the milk protein is preferably lactose-reduced or lactose-free.

Suitable digestible carbohydrates include maltodextrin, hydrolysed or modified starch or corn starch, glucose polymers, corn syrup, corn syrup solids, tapioca, sucrose, and glucose, or mixtures thereof. Generally digestible carbohydrates provide about 35% to about 75%, preferably about 45% to 70%, of the energy of the nutritional composition. Preferably the digestible carbohydrate is free from lactose.

Suitable lipids include rapeseed oil, sunflower seed oil, palm oil, soy oil, milk fat, corn oil and soy lecithin. Long-chain poly unsaturated fatty acids (LC-PUFA), especially omega-3 fatty acids such as docosahexaenoic acid (DHA), can be included in the lipid source because they have anti-inflammatory properties. Suitable sources of LC-PUFA are plant oils, marine plankton oils, fungal oils, and fish oils. The lipid source can also include medium chain triglycerides (MCT). Fractionated coconut oils are a suitable source of medium chain triglycerides. The lipid source preferably provides about 5% to about 25% of the energy of the nutritional composition; for example about 10% to 20%. The lipid content is preferably reduced because high fat diets can provoke IBS symptoms.

The nutritional composition preferably also includes vitamins and minerals. If the nutritional composition is intended to be a sole source of nutrition, it preferably includes a complete vitamin and mineral profile. Examples of vitamins include Vitamins A, B-complex (such as B1, B2, B6 and B12), C, D, E and K, niacin and acid vitamins such as pantothenic acid and folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 g/ml of lutein. Lycopene can be included in an amount from about 0.001 µg/ml to about 10 µg/ml, preferably about 0.0185 mg/ml to about 5 g/ml of lycopene. Beta-carotene can comprise from about 0.001 µg/ml to about 10 mg/ml, for example about 0.034 µg/ml to about 5 µg/ml of beta-carotene.

The nutritional composition can also contain various other conventional ingredients such as preservatives, emulsifying agents, thickening agents, buffers, fibres and probiotics, especially probiotics which can help to reduce symptoms in IBS patients (e.g. VSL #3, *B. infantis* 35624, *B. animalis* subsp. *lactis* BB-12, *B. lactis* Bi-07, *L. rhamnosus* GG, *L. rhamnosus* Lc705, *L. plantarum* DSM 9843, *L. plantarum* CECT7484, *L. plantarum* CECT7485, *L. acidophilus* NCFM, *L. fermenturn* CECT5716, *B. breve* Bb99, *Propionibacterium freundenreichii* ssp. *Shermanii* JS, *P. acidilactici* CECET7483, *Streptococcus faecium*), antioxidant/anti-inflammatory compounds including tocopherols, caroteinoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be in the form of a soluble powder, a liquid concentrate, or a ready-to-use formulation. Various flavours, fibres and other additives can also be present.

The nutritional composition can be prepared by any commonly used manufacturing techniques for preparing nutritional compositions in solid or liquid form. For example, the composition can be prepared from various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is also prepared by adding minerals, trace and ultra-trace minerals, thickening or suspending agents to water while heating and stirring. The resulting solution is held for 10 minutes with continued heat and agitation before adding carbohydrates (e.g., the neutral HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packaged to form an aseptically packaged nutritional composition. In this form, the nutritional composition can be in ready-to-feed or concentrated liquid form. Alternatively, the composition can be spray dried and processed and packaged as a reconstitutable powder.

When the nutritional product is a ready-to-feed nutritional liquid, the total concentration of one or more, neutral HMOs in the liquid, by weight of the liquid, is from about 0.002% to about 3.0%, including from about 0.005% to about 2%, including from about 0.05% to about 1.0%. When the nutritional product is a concentrated nutritional liquid, the total concentration of neutral HMOs in the liquid, by weight of the liquid, is from about 0.004% to about 6.0%, including from about 0.01% to about 4.0%, including from about 0.1% to about 2.0%.

Unit Dosage Forms

The synthetic composition of this invention can also be in a unit dosage form such as a capsule, tablet or sachet. For example, the composition can be formulated into single serve sachets containing the neutral HMOs, especially if higher doses are to be administered (e.g., more than 3 g). Alternative the composition can be in a tablet form comprising the human milk oligosaccharides, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQlO") and glutathione.

The unit dosage forms, especially those in sachet form, can also include various nutrients including macronutrients.

Administration Dosing

For improving the symptoms of co-morbid mental disorders in an IBS patient having suffering from stress, bacterial overgrowth, dysbiosis and/or an impaired mucosal barrier, the amount of neutral HMO(s) required to be administered to the patient will vary depending upon factors such as the risk and severity of the disease, the age of the patient, the form of the composition, and other medications being administered to the patient. However, the required amount can be readily determined by a medical practitioner and would generally be in the range of about 20 mg to about 30 g per day, preferably about 50 mg to about 20 g per day, or from about 100 mg to about 15 g per day, in certain embodiments from about 500 mg to about 10 g per day, preferably from about 1 g to about 7.5 g per day. During an initial treatment phase, the dosing can be higher, for example 100 mg to 30 g per day, preferably 500 mg to 15 g per day, more preferably 1 g to 10 g per day, in certain embodiments 2.5 g to 7.5 g per day. During a secondary prevention phase, the dosing can be reduced, for example, to 20 mg to 20 g per day, preferably to 100 mg to 10 g per day, more preferably to 500 mg to 7.5 g per day, in certain embodiments to 750 mg to 5 g per day.

EXAMPLES

Examples are now described to further illustrate the invention:

Example 1

Human Trial

A total of 300 male and female IBS patients are recruited to participate in the study. After a screening visit and run-in period of 1-2 weeks, the patients are selected. The patients are randomized into two groups, each of 150 patients, with one group consuming the treatment product and one group the placebo product for 8 weeks. The treatment product contains 5 grams of a combination of 2'-FL and LNnT while the control product contains 2 grams glucose. Both products are in powder form in identical sachets.

The patients are eligible to participate if: they are between 18 and 60 years of age; fulfill definition of IBS-D, IBS-C or IBS-A/M according to Rome IV criteria for IBS; have a global IBS-SSS score of >174 during the run-in period; and are able and willing to understand and comply with the study procedures. Patients are excluded if: they have participated in a clinical study one month prior to screening visit; they have abnormal results in the screening tests which are clinically relevant for study participation; any known gastrointestinal disease(s) that may cause symptoms or may interfere with the trial outcome, in particular lactose intolerance and coeliac disease; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 1 months prior to the study; consumed antibiotic drugs 1 months prior to the study; consumed on a regular basis any medication that might interfere with symptom evaluation 2 weeks prior to the study; and pregnant or lactating.

At the initial visit (screening), each patient is given both written and oral information about the study and the patient is asked to sign an informed consent form.

Patients are evaluated by a full review of clinical history and IBS diagnostic criteria is assessed. Part 1 of the IBS-SSS questionnaire is completed. Equipment for faecal sampling and cooling kits are distributed to the patient together with the Bristol Stool Form Scale (BSFS) and Bowel Movement Diary (BMD) to be filled in during the 7 days just prior to the second visit (beginning of intervention). Patients are asked to register their diet 3 days just prior to the second visit, and are reminded not to change their usual diet during the study.

At the second visit (beginning of intervention), eligibility criteria are checked and eligible subjects are randomised to the two arms in the trial. A physical examination is done. A number of questionnaires (GSRS-IBS, IBS-SSS, HADS, NRS-11, VSI, IBS-QOL and PHQ-15 scales) are answered. The questionnaires are:

GSRS-IBS: Gastrointestinal Symptom Rating Scale. This questionnaire includes 15 items covering five dimensions (abdominal pain, indigestion, reflux, diarrhoea, constipation) and uses a seven-graded Likert scale;
IBS-SSS: IBS severity scoring system;
HADS: Hospital Anxiety and Depression Scale;
NRS-11: Numerical Rating Scale;
VSI: Visceral Sensitivity Index
IBS-QoL: IBS-Quality of life (QoL)
PHQ-15: Patient Health Questionnaire scales Based on clinical symptoms and data from the questionnaires, patients are grouped into one of the three following categories: diarrhoea predominant (IBS-D), constipation predominant (IBS-C) or alternating/mixed (IBS-A/M). This enables allocation of patients from each subgroup into the intervention groups. Trial supplementation is distributed along with instructions on use of an electronic compliance diary. The faecal samples are collected and equipment for collecting new samples are distributed. Patients are reminded not to change their usual diet during the study. Diet records are collected, and patients are asked to register their diet for 3 days just prior to visit 3.

Patients with IBS-D and IBS-A/M, are tested for lactose intolerance and coeliac disease, if not done previously. Blood samples are collected for routine clinical chemistry and haematology and biomarker analysis. The serum from the blood samples is transferred to cryotubes and stored at −80° C. The following biomarkers are measured TNF-α, IL-1β, IL-8, IL-6, IL-12, IL-10, MIP-1β, hs-CRP, lipopolysaccharide binding protein, tryptase, antiflagellin, zonulin, histamine, prostaglandin 2, and cortisol. The faecal samples are stored at −80° C. until analysis. Microbiological analysis is performed on the faecal samples using the 16 S rRNA gene sequence.

The study runs for 8 weeks with the patients consuming either a placebo or a treatment product daily. Patients are instructed to consume the products in the morning with breakfast. Compliance is monitored through the interactive internet enabled system. Four weeks after commencement, there is an intermediate check. A physical examination is done and symptoms (as measured by GSRS-IBS, IBS-SSS, HADS, NRS-11, VSI, IBS-QOL and PHQ-15 scales) are reassessed. BSFS and BMD are collected and new forms, to be filled in daily during the intervention period, are distributed. Faecal samples and blood samples are collected and analysed as before, and equipment for collection of new faecal samples are distributed.

At the end of the intervention (8 weeks), each patient has a visit with the medical team. A physical examination is done and symptoms (as measured by GSRS-IBS, IBS-SSS, HADS, NRS-11, VSI, IBS-QOL and PHQ-15 scales) are reassessed. Trial supplementation products are collected to check compliance. Patients are asked about any adverse events and any changes in their usual medication. The BSFS and BMD are collected. Diet records are collected.

Faecal samples and blood samples are collected and analysed as before.

At this visit, the participants are asked if they wish to continue in an open label follow up study. Fifty percent of the participants continuing are given half the dose of the active product and the rest are not taking the product. The patients agreeing to continue are given equipment for faecal sample collection and for the patients continuing on active product, trial supplementation is distributed.

At the end of the study, the patients have a final visit where faecal samples are collected and symptoms (as measured by GSRS-IBS, IBS-SSS, HADS, NRS-11, VSI, IBS-QOL and PHQ-15 scales) are reassessed from the patients of the open label follow-up study and BSFS and BMD are collected. Additionally, they are asked about any adverse events.

For patients not participating in the open label follow up study, this visit will only be relevant if they have adverse events. This visit may be completed via telephone. The treatment patients report a reduction in pain/visceral sensitivity, a reduction in anxiety, a reduction in depression and an improvement in bowel movement as compared to the placebo group. The blood biomarker analysis indicates that the treatment patients have reduced levels of inflammatory markers, reduced gut permeability indicating an improved mucosal barrier, and reduced evidence of mast cell degranulation. The faecal analysis indicates that the treatment patients have reduced levels of bacterial overgrowth/dysbiosis and a higher level of bifidobacteria, in particular a *Bifidobacterium* of the *B. adolescentis* phylogenetic group. especially *Bifidobacterium adolescentis* and/or *Bifidobacterium pseudocatenulatum*.

Example 2

Nutritional Compositions

Ready to feed nutritional compositions are prepared from water, maltodextrin, corn syrup, sugar, milk protein concentrate, vegetable oil (canola, high oleic sunflower and corn), soy protein isolate, acacia gum, flavours, one or more, neutral HMOs, potassium citrate, magnesium phosphate, cellulose gel and gum, calcium carbonate, sodium ascorbate, soy lecithin, choline bitartrate, calcium phosphate, alpha-tocopheryl acetate, ascorbic acid, carrageenan gum, ferric pyrophosphate, flavours, sweeteners (Stevia), vitamin A palmitate, niacinamide, vitamin D3, calcium pantothenate, manganese sulphate, copper sulphate, pyridoxine hydrochloride, thiamine hydrochloride, beta carotene, riboflavin, chromium chloride, folic acid, biotin, potassium iodide, phytonadione, sodium selenite, sodium molybdate, vitamin B12.

The compositions each provide a nutritional supplement which is a good source of protein, low in fat, vitamins, minerals and antioxidants, and meets FODMAP criteria. Further, the compositions contain neutral HMOs which are able to promote the growth of beneficial intestinal bacteria, modulate chronic inflammation, improve mucosal barrier integrity and reduce anxiety and depression.

Example 3

Capsule Compositions

Capsules are each prepared by filling about 1 g of one or more, neutral HMOs into a 000 gelatine capsule using a filing machine. The capsules are then closed. The neutral HMOs are in free flowing, powder form.

The invention claimed is:

1. A method for treating a co-morbid mental disorder in a patient with irritable bowel syndrome (IBS), comprising orally administering to the patient an effective amount of a synthetic composition comprising one or more neutral human milk oligosaccharides (HMOs), wherein the amount is effective to increase the abundance of *Bifidobacterium* of the *B. adolescentis* phylogenetic group in the IBS patient.

2. The method according to claim 1, wherein the co-morbid mental disorder is depression.

3. The method according to claim 1 wherein the patient is administered a higher amount of the one or more neutral HMOs for an initial treatment period, followed by a lower amount of the one or more neutral HMOs, for a maintenance period.

4. The method according to claim 1, wherein the neutral HMO is selected from the group consisting of 2'-fucosyllactose (2'-FL), 3-fucosyllactose (3-FL), difucosyllactose (DFL), lacto-N-tetraose (LNT), lacto-N-neotetraose (LNnT) and lacto-N-fucopentaose I (LNFP-I).

5. The method according to claim 1, wherein the synthetic composition comprises one or more neutral non-fucosylated HMOs and one or more neutral fucosylated HMOs.

6. The method according to claim 5 wherein the synthetic composition comprises 2'-FL and/or DFL, and LNnT and/or LNT.

7. The method according to claim 1, wherein the *Bifidobacterium* of the *B. adolescentis* phylogenetic group is *Bifidobacterium adolescentis* and/or *Bifidobacterium pseudocatenulatum*.

8. The method of claim 1, wherein the patient exhibits one or more symptoms of stress, bacterial overgrowth, dysbiosis, or impaired mucosal barrier.

9. A method for treating a co-morbid mental disorder in a patient with irritable bowel syndrome (IBS), comprising orally administering to the patient an effective amount of a synthetic composition comprising one or more neutral human milk oligosaccharides (HMOs),
wherein the patient is administered a higher amount of the one or more neutral HMOs for an initial treatment period, followed by a lower amount of the one or more neutral HMOs, for a maintenance period,
wherein the initial treatment period comprises administering 5 g to 10 g per day of the one or more neutral HMOs.

10. A method for treating a co-morbid mental disorder in a patient with irritable bowel syndrome (IBS), comprising orally administering to the patient an effective amount of a synthetic composition comprising one or more neutral human milk oligosaccharides (HMOs),
wherein the patient is administered a higher amount of the one or more neutral HMOs for an initial treatment period, followed by a lower amount of the one or more neutral HMOs, for a maintenance period,
wherein the maintenance period comprises administering 1 g to 5 g per day of the one or more neutral HMOs.

11. The method according to claim 3, wherein the initial treatment period is one to eight weeks.

12. The method according to claim 3, wherein the maintenance period is at least one month.

13. The method according to claim 6 wherein the synthetic composition comprises 2'-FL and LNT.

14. The method according to claim 6 wherein the synthetic composition comprises 2'-FL, DFL and LNnT.

15. The method according to claim 1, wherein the synthetic composition further comprises a diluent, excipient, antioxidant, lubricant, colorant, binder, disintegrant or a mixture thereof.

16. The method according to claim 1, wherein the synthetic composition is a nutritional composition further comprising folic acid.

17. The method according to claim 1, wherein the synthetic composition consists of one or more neutral HMOs.

18. The method according to claim 17, wherein the neutral HMO is selected from the group consisting of 2'-fucosyllactose (2'-FL), 3-fucosyllactose (3-FL), difucosyllactose (DFL), lacto-N-tetraose (LNT), lacto-N-neotetraose (LNnT) and lacto-N-fucopentaose I (LNFP-I).

19. The method according to claim 17, wherein the one or more neutral HMOs consists of two or more neutral HMOs consisting of one or more neutral non-fucosylated HMOs and one or more neutral fucosylated HMOs.

20. The method according to claim 19 wherein the synthetic composition consists of 2'-FL and LNT.

21. The method according to claim 19 wherein the synthetic composition consists of 2'-FL, DFL and LNnT.

* * * * *